United States Patent [19]

Yoshisato et al.

[11] 4,330,633

[45] May 18, 1982

[54] SOLID ELECTROLYTE

[75] Inventors: Eishin Yoshisato; Shizuo Azuma, both of Iwakuni; Teizo Yamaji, Yamaguchi, all of Japan

[73] Assignee: Teijin Limited, Osaka, Japan

[21] Appl. No.: 231,269

[22] Filed: Feb. 3, 1981

[30] Foreign Application Priority Data

Aug. 15, 1980 [JP] Japan ................................ 55-111787
Aug. 15, 1980 [JP] Japan ................................ 55-111788

[51] Int. Cl.$^3$ ....................... C04B 35/00; C04B 35/50
[52] U.S. Cl. ........................................ 501/152; 501/1; 264/65
[58] Field of Search ................ 252/62.2; 429/30, 103, 429/104, 193; 204/195 S; 106/39.5, 73.2; 501/1, 152; 264/65

[56] References Cited

U.S. PATENT DOCUMENTS 4,151,060  4/1979  Isenberg ........................ 204/195 S

*Primary Examiner*—O. R. Vertiz
*Assistant Examiner*—Mark Bell
*Attorney, Agent, or Firm*—Sherman & Shalloway

[57] ABSTRACT

A solid electrolyte having high electron conductivity and high oxide ion conductivity, which is composed of a sintered body consisting substantially of (a) an oxide of cobalt, (b) an oxide of at least one metal selected from strontium and lanthanum, and (c) an oxide of at least one metal selected from bismuth and cerium. This solid electrolyte is useful for selectively separating oxygen from a gaseous atmosphere having a high oxygen partial pressure into a gaseous atmosphere having a low oxygen partial pressure.

10 Claims, No Drawings

SOLID ELECTROLYTE

This invention relates to a novel solid electrolyte. Specifically, it relates to an inorganic solid electrolyte having electron conductivity and oxide ion conductivity which is composed of a sintered body consisting substantially of the oxides of three different kinds of metal including cobalt, and to a use of the aforesaid solid electrolyte as an oxygen-permselective membrane.

In recent years, there has been a marked advance in mixture separating techniques by a membrane method, an adsorption method, etc., and some of them have already gained commercial acceptance. Separation techniques now in commercial practice, however, pertain largely to liquid-liquid separation and liquid solid separation as in desalination of sea water, treatment of industrial wastes and concentration of foodstuffs, and little has been achieved in gas-gas separation, i.e. the separation of at least one gaseous component from a mixture of at least two gases. Various reasons may be assigned to the difficultly with gas-gas separation. For example, in the case of the membrane method, a membrane which is selectively permeable to a specified gas and scarcely permits permeation of other gases has not been available, and therefore membrane separation must be carried out in a multiplicity of stages. Such a process naturally requires an excessively large-sized apparatus. Moreover, since the amount of gas permeated is small, a large quantity of gas cannot be obtained.

Heretofore, organic polymeric membranes have mainly been suggested for use as gas-gas separation membranes. For example, a method for separating oxygen in the air using a membrane of an organopolysiloxane/polycarbonate copolymer was proposed [Journal of Membrane Science, 1, 99-108, (1976)]. The concentration of oxygen separable from the air using this organic polymeric membrane is about 30 to 40%, and the membrane has poor permselectivity. Furthermore, since organic polymeric membranes used in gas separation have poor heat resistance, they cannot be used for treatment of high-temperature gaseous mixtures, for example separation of oxygen from waste gases of industrial furnaces such as blast furnaces and glass melting furnaces.

On the other hand, U.S. Pat. No. 3,310,381 discloses an oxygen-enriching method based on adsorption and desorption using BaO. West German Patent (OLS) No. 2,450,605 discloses an adsorption-desorption method using a metal oxide such as Ce-Pr oxide or molecular sieves. Such adsorption-desorption methods are economically disadvantageous because they require oxygen adsorbing and desorbing steps and the equipment becomes complex.

U.S. Pat. No. 3,400,054 discloses a method for separating oxygen from an oxygen-containing gaseous mixture using a solid electrolyte of the formula $(ZrO_2)_{1-x}(CaO)_x$ ($x = 0.05$–$0.3$). This method is based on the theory that by utilizing the oxide ion conductivity of the solid electrolyte, oxygen in the gaseous mixture is electrochemically permeated through it. Specifically, an oxide ion resulting from ionization on one surface of the solid electrolyte is caused to migrate through the electrolyte, and is discharged on the other surface to give an oxygen gas. Ionization and discharge of oxygen required for this method are performed by means of electrically short-circuited electrodes through an external circuit secured to both surfaces of the solid electrolyte. Accordingly, this method has the defect that because ionization and discharge of oxygen are effected only at a site at which the three phases, i.e. the solid electrolytes, electrode material and oxygen gas, contact each other, the effective area of the solid electrolyte membrane is small, the amount of oxygen gas permeated is small, and the electrode and the electrolyte undergo deterioration with time owing to contact. Furthermore, the complexity of the apparatus used makes the method economically disadvantageous. The need for securing electrodes and external circuits in the oxygen-separating method disclosed in the aforesaid U.S. patent is due to the fact that the electron conductivity of the solid electrolyte used is much lower than its oxide ion conductivity.

It is an object of this invention therefore to provide a solid electrolyte having both high electron conductivity and high oxide ion conductivity and excellent heat resistance which does not require an electrode and an external circuit.

Another object of this invention is to provide a process for producing such a solid electrolyte.

Still another object of this invention is to provide a method for easily separating oxygen selectively from an oxygen-containing gaseous mixture using a membrane formed of such a solid electrolyte.

Other objects and advantages of this invention will become apparent from the following description.

According to this invention, there is provided a solid electrolyte having electron conductivity and oxide ion conductivity, which is composed of a sintered body consisting substantially of
   (a) an oxide of cobalt,
   (b) an oxide of at least one metal selected from strontium and lanthanum, and
   (c) an oxide of at least one metal selected from bismuth and cerium.

The solid electrolyte of this invention is characterized by the fact that it is not a mere mechanical mixture of the three metal oxide components but a compact sintered body in which the three metal oxide components are bonded to each other by some chemical bonds such as metallic bonds, covalent bonds, ionic bonds and molecular bonds, and that it has both high electron conductivity and high oxide ion conductivity.

The term "electron conductivity", as used in the present specification and the appended claims, denotes conductivity attributed to electrons and/or electron holes, and the term "oxide ion conductivity", as used herein, denotes conductivity attributed to an oxide ion. These conductivites can be determined as follows:

A cylindrical solid electrolyte sample, 5 mm in diameter and 10 mm in length, is used, and its total conductivity (electron conductivity plus oxide ion conductivity) is determined by measuring its specific resistance (ohm-cm) by an ordinary ac bridge method or dc four-probe method. The dc four-probe method is used for a conductivity of at least 1 ohm$^{-1}$·cm$^{-1}$, and the ac bridge method, for a conductivity of less than 1 ohm$^{-1}$·cm$^{-1}$.

According to the dc four-probe method, the resistance of the sample is determined by wrapping two lead wires made of platinum or silver around the periphery of the sample at an interval of 7 to 8 mm, passing an electric current of usually 1 to 500 mA across the two ends of the sample, and measuring the potential difference between the two lead wires. The ac bride method is carried out by using a high-frequency bridge having an ordinary equivalent circuit. Unless otherwise indicated, all resistance values in this application are measured at 10 KHz.

From the total conductivity of the sample determined as above, its oxide ion conductivity is calculated in accordance with the following equation.

$$\text{Oxide ion conductivity} = (\text{total conductivity}) \times t \quad (1)$$

wherein t represents the ratio, to an oxygen concentration potential difference (theoretical value) calculated by an oxygen concentration potential method at a given oxygen pressure difference, of an oxygen concentration potential difference measured when the same oxygen pressure difference is provided on both sides of the sample.

The electron conductivity of the sample can be obtained by subtracting the oxide ion conductivity calculated by equation (1) from the total conductivity measured.

When the electron conductivity of the solid electrolyte is at least about 10 times as high as its oxide ion conductivity, polarization increases, and the oxygen concentration potential difference is difficult to measure. In such a case, the oxide ion conductivity is determined by the following equation (2) by measuring the permeating velocity V (cc/sec.cm$^2$) of oxygen electrochemically passing from a high oxygen pressure side to a low oxygen pressure side through a membrane of the solid electrolyte.

$$V = 2.88 \times 10^{-6} \frac{\sigma_O}{d} T \log \frac{P_1}{P_2} \quad (2)$$

wherein $\sigma_O$ is the oxide ion conductivity (ohm$^{-1}$·cm$^{-1}$),
d is the thickness of the membrane (cm),
T is the absolute temperature (°K.),
P$_1$ is the oxygen pressure of the high oxygen pressure side, and
P$_2$ is the oxygen pressure of the low oxygen pressure side.

The electron conductivity and oxide ion conductivity slightly vary depending upon the measuring temperature. Unless otherwise specified, all electron and oxide ion conductivities mentioned in the present application are those measured at a temperature of 800° C.

The solid electrolyte of this invention has a very high electron conductivity of generally at least $10^{-2}$ ohm$^{-1}$·cm$^{-1}$, preferably at least $10^{-1}$ ohm$^{-1}$cm$^{-1}$, more preferably 1 to $10^3$ ohm$^{-1}$·cm$^{-1}$ and a very high oxide ion conductivity of at least $10^{-4}$ ohm$^{-1}$·cm$^{-1}$, preferably $10^{-3}$ ohm$^{-1}$·cm$^{-1}$, more preferably $10^{-2}$ to 1 ohm$^{-1}$·cm$^{-1}$ although these conductivities slightly vary depending upon the types or proportions of the metal oxides constituting it. In this regard, the solid electrolyte of this invention is essentially distinguished from similar solid electrolytes proposed heretofore.

Furthermore, the electron conductivity of the solid electrolyte of this invention is conveniently balanced with its oxide ion conductivity, and the ratio of the electron conductivity (ohm$^-$·cm$^{-1}$) to the oxide ion conductivity (ohm$^{-1}$·cm$^{-1}$) is generally in the range of from $10^{-2}$ to $10^7$, preferably from $10^{-1}$ to $10^6$, more preferably from 1 to $10^5$.

The sintered body which provides the solid electrolyte having such a high electron and oxide ion conductivity consists substantially of (a) an oxide of cobalt,
(b) an oxide of strontium and/or an oxide of lanthanum, and
(c) an oxide of bismuth and/or an oxide of cerium.

It is to be understood that in the following description, the metal oxide composition of the sintered body is expressed in terms of the metals in the metal oxides. For example, a sintered body consisting substantially of cobalt oxide, strontium oxide and bismuth oxide is described as a Co-Sr-Bi type sintered body.

The solid electrolyte of this invention may be composed of a sintered body consisting of any one of the following metal oxide combinations.

Co—Sr—Bi,
Co—La—Bi,
Co—Sr—Ce,
Co—La—Ce,
Co—Sr—La—Bi,
Co—Sr—La—Ce,
Co—Sr—Bi—Ce,
Co—La—Bi—Ce, and
Co—Sr—La—Bi—Ce.

The solid sintered body of the invention can give a solid electrolyte having high electron and oxide ion conductivity when it contains the metal oxide components (a), (b) and (c) in the proportions tabulated below.

| Metal oxide component | Proportion (*) |
| --- | --- |
| Cobalt oxide | 5–85 mole % (10–80 mole %) |
| Strontium and/or lanthanum oxide | 2–70 mole % (3–60 mole %) |
| Bismuth oxide and/or cerium oxide | 13–80 mole % (15–70 mole %) |

(*) The parenthesized figures show preferred ranges.

When the metal oxide component (b) consists of strontium oxide and lanthanum oxide, the ratio between the two is not critical and can be varied widely according to the properties required of the final solid electrolyte, etc. Generally, the suitable mole ratio of strontium oxide to lanthanum oxide is from 0.01 to 100, preferably from 0.1 to 50.

When the metal oxide component (c) consists of bismuth oxide and cerium oxide, the ratio between them is neither critical and can be varied widely according to the properties required of the final solid electrolyte, etc. Advantageously, the bismuth oxide/cerium oxide mole ratio is set generally at 0.01 to 100, preferably at 0.1 to 50, as in the component (b).

The preferred ratio of the metal oxide components (a), (b) and (c) in the sintered body in accordance with this invention varies depending upon the metal oxides selected as the components (b) and (c). Some typical examples are given below.

| | | |
| --- | --- | --- |
| (A) | Co—La—Bi type | |
| | Cobalt oxide | 15 to 75 mole % |
| | Lanthanum oxide | 13 to 45 mole % |
| | Bismuth oxide | 17 to 50 mole % |
| (B) | Co—Sr—Ce type | |
| | Cobalt oxide | 15 to 40 mole % |
| | Strontium oxide | 40 to 55 mole % |
| | Cerium oxide | 15 to 40 mole % |
| (C) | Co—Sr—Bi type | |
| | Cobalt oxide | 10 to 40 mole % |

|     |                | |
|-----|----------------|-----------------|
|     | Strontium oxide | 5 to 40 mole %  |
|     | Bismuth oxide   | 35 to 70 mole % |
| (D) | Co—La—Ce type   |                 |
|     | Cobalt oxide    | 10 to 40 mole % |
|     | Lanthanum oxide | 10 to 40 mole % |
|     | Cerium oxide    | 30 to 70 mole % |
| (E) | Co—La—Sr—Bi type |                |
|     | Cobalt oxide    | 15 to 70 mole % |
|     | Lanthanum oxide | 1 to 40 mole %  |
|     | Strontium oxide | 1 to 40 mole %  |
|     | Bismuth oxide   | 25 to 50 mole % |
| (F) | Co—La—Sr—Ce type |                |
|     | Cobalt oxide    | 10 to 40 mole % |
|     | Lanthanum oxide | 1 to 35 mole %  |
|     | Strontium oxide | 1 to 35 mole %  |
|     | Cerium oxide    | 30 to 70 mole % |

The sintered body in accordance with the invention may consist only of the metal oxide components (a), (b) and (c). Or it may further comprise a reinforcing material and/or a binder material, such as silica, alumina, silica-alumina, magnesia and silica-magnesia. Such an additional material may be used in a proportion of at most 5% by weight, preferably 1 to 3% by weight, based on the weight of the sintered body.

A Co-La-Bi type sintered body consisting substantially of cobalt oxide, lanthanum oxide and bismuth oxide is an especially preferred solid electrolyte in accordance with the invention, and next comes a Co-Sr-Ce type sintered body consisting substantially of cobalt oxide, strontium oxide and cerium oxide.

It has been ascertained that in the sintered body of the invention, the three metal oxide components (a), (b) and (c) are bonded into a compact mass by some chemical bonding forces, and it has a crystal structure inherent to a given combination of the metal oxide components constituting the sintered body and exhibits an X-ray diffraction pattern inherent thereto. Some typical sintered bodies of the invention have the following characteristic peaks in X-ray diffraction (Cu-K$\alpha$ rays).

| (A) | Co—La—Bi type |     |
|-----|---------------|-----|
|     | Diffraction angle ($2\theta$) | Relative intensity (%; the peak intensity at $2\theta = 29.1$ is taken as 100%) |
|     | 25.6 | 1–25 |
|     | 26.2 | 1–25 |
|     | 28.6 | 10–65 |
|     | 29.1 | 100 |
|     | 30.2 | 5–40 |
|     | 32.8 | 1–120 |
|     | 33.3 | 1–120 |
|     | 40.6 | 0.1–50 |
|     | 44.8 | 1–40 |
|     | 47.5 | 1–100 |
| (B) | Co—Sr—Ce type |     |
|     | Diffraction angle ($2\theta$) | Relative intensity (%; the peak intensity at $2\theta = 29.4$ is taken as 100%) |
|     | 29.0 | 5–40 |
|     | 29.4 | 100 |
|     | 29.7 | 5–40 |
|     | 32.8 | 10–100 |
|     | 42.0 | 10–70 |
|     | 47.3 | 1–30 |
|     | 51.7 | 5–40 |
|     | 52.5 | 10–50 |
|     | 58.5 | 1–20 |
| (C) | Co—Sr—Bi type |     |
|     | Diffraction angle ($2\theta$) | Relative intensity (%; the peak intensity at $2\theta = 28.2$ is taken as 100%) |
|     | 26.1 | 1–20 |
|     | 26.7 | 5–50 |
|     | 28.2 | 100 |
|     | 28.8 | 10–200 |
|     | 30.0 | 5–100 |
|     | 30.4 | 5–100 |
|     | 36.4 | 1–50 |
|     | 45.8 | 1–70 |
|     | 49.4 | 1–50 |
|     | 54.8 | 1–70 |
| (D) | Co—La—Ce type |     |
|     | Diffraction angle ($2\theta$) | Relative intensity (%; the peak intensity at $2\theta = 27.9$ is taken as 100%) |
|     | 27.9 | 100 |
|     | 32.2 | 1–50 |
|     | 32.8 | 1–50 |
|     | 33.2 | 1–50 |
|     | 46.3 | 5–100 |
|     | 47.4 | 1–30 |
|     | 54.9 | 5–100 |
|     | 58.9 | 1–30 |
|     | 74.5 | 1–30 |
|     | 85.8 | 1–30 |
| (E) | Co—La—Sr—Bi type |  |
|     | Diffraction angle ($2\theta$) | Relative intensity (%; the peak intensity at $2\theta = 28.4$ is taken as 100%) |
|     | 26.6 | 5–50 |
|     | 28.4 | 100 |
|     | 28.7 | 10–400 |
|     | 30.3 | 5–100 |
|     | 33.1 | 1–150 |
|     | 40.6 | 1–30 |
|     | 47.3 | 1–100 |
|     | 58.8 | 5–50 |
| (F) | Co—La—Sr—Ce type |  |
|     | Diffraction angle ($2\theta$) | Relative intensity (%; the peak intensity at $2\theta = 33.1$ is taken as 100%) |
|     | 28.5 | 20–200 |
|     | 33.1 | 100 |
|     | 40.8 | 1–30 |
|     | 47.4 | 20–200 |
|     | 56.2 | 10–100 |
|     | 59.1 | 10–50 |

The sintered body in accordance with the invention is very compact, and has a density of generally at least 5 g/cm$^3$, preferably 5.5 to 9 g/cm$^3$, more preferably 6 to 8 cm$^3$. When the permeability of the sintered body of the invention to nitrogen gas is measured by a method which comprises passing an argon gas at a flow rate of 30 cc (STP)/min. at 800° C. through the inside of a bottomed cylindrical sample of the sintered body having a thickness of 1 mm, and outside diameter of 11.7 mm and a height of 12 mm while contacting the outside surface of the cylindrical sample with nitrogen gas under 1 kg/cm$^2$·G and determining the concentration of nitrogen gas in the argon gas flow by gas chromatography, the sintered body of the invention has been found to be substantially impermeable to nitrogen gas.

The density of the sintered body is determined by measuring the weight of a cylindrical sintered body sample having a diameter of 5 mm and a length of 10 mm, and dividing the weight by its volume.

The solid electrolyte of the invention having these characteristic properties can be produced in accordance with a customary sintering technique by a process which comprises firing a mixture consisting substantially of (i) cobalt, its oxide or a cobalt compound capable of being decomposed to cobalt oxide under the firing conditions, (ii) a metal selected from strontium and lanthanum, an oxide of the metal, or a compound of the metal capable of being decomposed to an oxide of the metal under the firing conditions, and (iii) a metal selected from bismuth and cerium, an oxide of the metal, or a compound of the metal capable of being decomposed to an oxide of the metal under the firing condition, if required in an oxidizing atmosphere.

Examples of the compounds of metals capable of being decomposed to oxides of the metals (i.e., cobalt oxide, strontium oxide and/or lanthanum oxide, and bismuth oxide and/or cerium oxide) under the firing conditions to be described include inorganic acid salts, for example carbonates such as cobalt carbonate, strontium carbonate, lanthanum carbonate, and cerium carbonate), nitrates such as cobalt nitrate, strontium nitrate, lanthanum nitrate, bismuth nitrate, cerium nitrate, and sulfates such as cobalt sulfate, strontium sulfate, bismuth sulfate, lanthanum sulfate and cerium sulfate; organic acid salts, for example acetates such as cobalt acetate, strontium acetate, lanthanum acetate, bismuth acetate and cerium acetate and oxalates such as cobalt oxalate, strontium oxalate, lanthanum oxalate, bismuth oxalate and cerium oxalate; hydroxides such as cobalt hydroxide, strontium hydroxide, lanthanum hydroxide, bismuth hydroxide and cerium hydroxide; and halides such as fluorides (e.g., strontium fluoride) and chlorides (e.g., cobalt chloride, lanthanum chloride and cerium chloride).

Among these metal compounds, cobalt nitrate, cobalt carbonate, cobalt hydroxide and strontium carbonate can be heat-decomposed even in the absence of oxygen to the corresponding metal oxides under the firing conditions. Hence, when these metal oxides are used as starting materials, the firing may be carried out in the absence of oxygen. On the other hand, when the acetates, oxalates and halides are used as starting materials, the firing should be performed in an oxidizing atmosphere.

The use of an oxidizing atmosphere is neither essential in firing the metal oxides as starting materials. But when the metals themselves are used as starting materials, the firing must be carried out in an oxidizing atmosphere.

The starting materials (i), (ii) and (iii) can be mixed in stoichiometrical amounts corresponding nearly to the proportions of the metal oxide components (a), (b) and (c) in the desired sintered body.

The starting materials (i), (ii) and (iii) need not to be completely pure, and may contain impurities in such small amounts as will not substantially affect the conductivity of the resulting sintered body.

The mixture of the starting materials (i), (ii) and (iii) may be prepared, for example, by (1) simply mixing powders of the metals, metal oxides or metal compounds mechanically by means of a ball mill, etc; (2) dissolving water-soluble compounds of the respective metals in water in desired concentrations, treating the solution with sodium carbonate or a metal-free alkali such as ammonia to co-precipitate insoluble metal compounds; or (3) forming an alloy of the metals when the metals are used as the starting materials. A suitable method may be selected from the above-exemplified methods in consideration of the availability of the starting materials, the economy of the operation, etc.

In order to improve the moldability of the starting mixture and to reinforce and bind the resulting sintered body, there may be incorporated additives, for example inorganic binders such as silica, alumina, silica-alumina, magnesia and silica-magnesia, and organic binders such as starch, glycerol, carbowax, polyvinyl alcohol, carboxymethyl cellulose, dextrin and wax emulsion. The suitable amount of these additives is generally up to 5% by weight, preferably 1 to 3% by weight, based on the weight of the mixture.

The starting mixture described above is then molded into a desired shape in a customary manner. The molding may be performed by press-forming the starting mixture into a desired shape such as a rod, pellet, plate or sheet by a wet or dry process, or by mechanically processing (cutting, polishing, etc.) the pellet or sheet so press-formed. When the resulting sintered body is to be used as an ultrathin oxygen-permselective membrane, the mixture may be applied as a thin layer to a heat-resistant porous support. Examples of the support may include a porous plate or sintered body of a metal such as stainless steel or bronze, a sintered body of a porous oxide such as porous silica alumina, porous alumina or porous magnesia, a sintered body of a nitride such as boron nitride, and a sintered body of a carbide such as silicon carbide.

Application of the starting mixture to the porous support may be effected by a method comprising forming the mixture into a paste using water and coating the paste on the support, a vacuum-deposition method, a reactive sputtering method, a chemical vapor-phase deposition method, a chemical spraying method, or a method involving oxidizing a coating of an alloy of the respective metals.

The molded mixture is then fired. Generally, the firing is carried out in an oxidizing atmosphere, for example in the air. Although an oxidizing atmosphere is not necessary when the aforesaid starting materials do not requires the oxidizing atmosphere, it is generally preferred to use it even in this case.

The firing can be carried out under temperature and time conditions in which the starting metal oxides or the metal oxides formed as a result of firing react with each other to produce a sintered state.

The firing temperature may be varied depending upon the types of the starting materials used, the degree of firing, etc. Advantageously, the firing temperature is generally about 400° C. to about 1400° C., preferably about 500° C. to about 1300° C. The firing time is neither critical, and may be varied widely depending upon the types of the starting materials, the size of the molded mixture, etc. Usually, the firing is preferably carried out for 0.5 to 20 hours.

Under these conditions, the firing may be carried out in an ordinary firing device such as an electrical furnace, gas furnace, heavy oil furnace, etc. while if desired, feeding an oxygen-containing gas such as air or an inert gas.

The firing may be performed by subjecting the molded starting mixture directly to high temperatures (about 400° to about 1400° C.) which induce sintering of the mixture. Generally, however, it is advantageous to raise the temperature gradually from a lower temperature of, for example, about 20 to about 100° C. to the aforesaid sintering temperatures. The temperature elevation at this time may be performed continuously or intermittently. Alternatively, the molded starting mixture may be pre-fired. Pre-firing is beneficial particularly when a mixture (e.g., coprecipitate) of metal compounds capable of being converted to the metal corresponding metal oxides under the firing conditions is used as a starting material. It may be carried out either before or after the molding of the starting mixture. The pre-firing may be carried out at a temperature of generally about 200° to about 500° C., preferably about 250° to about 400° C., for about 0.5 to about 20 hours, preferably in an oxidizing atmosphere.

When it is desired to obtain a sintered body having increased compactness, it is possible to cool the resulting sintered body, pulverize it, again press-form the powder under a high pressure of preferably about 10 to about 4,000 kg/cm², and then again fire the molded mixture. By repeating this procedure, a product of higher compactness can be obtained.

The solid electrolyte so produced has high electron conductivity and oxide ion conductivity and very good oxygen permselectivity. For example, the permeability (amount permeated) and purity of oxygen obtained through a solid electrolyte composed of a sintered body consisting of 25 mole% of cobalt oxide, 32.5 mole% of lanthanum oxide and 42.5 mole% of bismuth oxide are $3.3 \times 10^{-3}$ (STP)/sec.cm², and 100% ($O_2$), respectively, when they are measured under the following conditions.

A bottomed cylindrical sample of the sintered body, having a thickness of 1 mm, an outside diameter of 11.7 mm and a height of 12 mm, is prepared. An argon gas is caused to flow through the inside of the sample at a flow rate of 30 cc (STP)/min. at 800° C. while contacting the outside surface of the cylinder with the air. The concentration of oxygen and the presence of other gases in the argon gas flow are determined by gas chromatography.

The solid electrolyte provided by this invention is suitable as a material for an oxygen permselective membrane. When the solid electrolyte of the invention is used as an oxygen perm-selective membrane, it is advantageously used as a thin film having a thickness of generally $10^{-3}$ to $10^4$ microns, preferably $10^{-2}$ to $5 \times 10^3$ microns, more preferably $10^{-1}$ to $10^3$ microns. An example of such a thin membrane is a solid electrolyte composite membrane obtained by firing under the aforesaid conditions the starting mixture applied to a porous support as stated hereinabove. A relatively thick membrane may also be prepared by shaving or polishing the sintered body obtained in the form of a pellet, plate or sheet as described hereinabove. When an ultrathin membrane is desired, the powder of the sintered body produced as above is flame-sprayed in an acetylene or plasma jet flame onto a porous support to apply the sintered body to the porous support in ultrathin film form and to form a composite membrane.

Oxygen may be selectively separated from an oxygen-containing gaseous mixture using the solid electrolyte membrane by providing two gaseous atmospheres having a difference in oxygen partial pressure through the membrane and heating the membrane to a temperature sufficient for the solid electrolyte to exhibit oxide ion conductivity, whereby oxygen in a gaseous atmosphere having a higher oxygen pressure migrates electrochemically through the membrane toward the other gaseous atmosphere having a low oxygen pressure and is thus separated and received in the latter.

The temperature at which the solid electrolyte exhibits oxide ion conductivity differs depending upon the types and proportions of the metal oxides constituting the solid electrolyte. The heating should be performed to a temperature of generally at least 400° C., preferably to 500° to 1200° C., more preferably to 600° to 1000° C.

Heating of the membrane to the aforesaid temperature may be carried out, for example, by (1) heating it directly with an electrical heater, (2) indirectly heating it by external heat transmission using a high temperature gas such as a high-temperature combustion gas or a high-temperature exhaust gas, (3) pre-heating a gas to be subjected to separation treatment and heating the membrane by the heat of the pre-heated gas, or (4) a combination of at least two of the methods (1) to (3).

It should be understood that the term "gaseous mixture having a low oxygen partial pressure" denotes a gaseous mixture ranging from a gaseous mixture completely free from oxygen to a gaseous atmosphere having an extremely low gas concentration close to complete vacuum.

There are various available embodiments in forming two gaseous atmospheres having a difference in the partial pressure of oxygen. For example, the two gaseous atmospheres may be provided by a method which comprises partitioning two communicating chambers air-tight by the aforesaid membrane and exposing one of the chambers to the atmospheric air while reducing the pressure of the other, or a method which comprises supplying pressurized air to one of the chambers and maintaining the other at atmospheric or reduced pressure. By using the above process, only oxygen selectively permeates electrochemically through the membrane and oxygen gas having a high purity can be obtained in the chamber having a low oxygen partial pressure. When it is desired to simply separate oxygen from an oxygen-containing gaseous mixture or obtain oxygen as a mixture with another gas not requiring a high oxygen concentration, it is possible to move oxygen alone from one chamber to the other by continuously feeding a gas of a low oxygen concentration from one chamber to the other while maintaining both chambers at the same pressure, for example at atmospheric pressure.

The solid electrolyte of this invention can be used, for example, for selective separation of oxygen from the air, separation or removal of oxygen in high-temperature steam decomposition, and also as an electrode material such as an electrode on the air pole side of high-temperature solid electrolyte fuel cells.

While conventional solid electrolytes have oxide ion conductivity alone and for use in oxygen separation, electron conductivity must be imparted thereto by, for example, providing an electrode and an external circuit on both sides of the solid electrolyte, the solid electrolyte membrane of this invention has the advantage that it has both electron and oxide ion conductivity, does not particularly require an electrode nor an external circuit and can be used as such as an oxygen separating membrane. Furthermore, the electrolyte of this invention gives oxygen of higher purity than conventional organic polymeric membranes. Moreover, since it has excellent heat resistance, it can be used at high temperatures and can be used for treatment of high-temperature gases.

The following Examples illustrate the present invention more specifically. All parts in these Examples are by weight.

EXAMPLE 1

Lanthanum oxide ($La_2O_3$; 2.12 parts), 3.96 parts of bismuth oxide ($Bi_2O_3$) and 2.49 parts of cobalt acetate [$Co(OCOCH_3)_2.4H_2O$] where pulverized and mixed in a mortar. The mixture was fired at 600° C. for 1 hour. The fired mixture was pulverized and mixed, and press-formed at 500 kg/cm², and further fired at 930° C. for 8 hours. The sintered body obtained was further pulverized and mixed, press-formed again at 2 tons/cm², and fired at 930° C. for 10 hours in the air to form a sintered body having a density of 6.9 g/cm² and the X-ray (Cu-Kα) diffraction pattern shown in Table 1. The sintered body was a solid electrolyte having an electron conductivity of 25 ohm$^{-1}$·cm$^{-1}$ and an oxide ion conductivity of $1.5 \times 10^{-1}$ ohm$^{-1}$·cm$^{-1}$.

A bottomed cylindrical sample of the solid electrolyte having an outside diameter of 11.7 mm, an inside diameter of 10.7 mm, a height of 12 mm and a thickness of 1 mm, was prepared. An argon gas was caused to flow through the inside of the sample at a flow rate of 30 cc (STP)/min. while keeping its outside in contact with the air. The sample was heated to 800° C. The oxygen concentration of the argon gas flow was determined by gas chromatography. It was ascertained that oxygen permeated through the sample at $3.3 \times 10^{-3}$ cc (STP)/sec·cm².

TABLE 1

| Diffraction angle (2θ) | Relative intensity (%; the peak intensity at 2θ = 29.1 is taken as 100%) |
| --- | --- |
| 25.6 | 17 |
| 26.2 | 17 |
| 28.6 | 55 |
| 29.1 | 100 |
| 30.2 | 32 |
| 32.8 | 30 |
| 33.3 | 30 |
| 40.6 | 9 |
| 44.8 | 17 |
| 47.5 | 17 |

EXAMPLE 2

Strontium nitrate [Sr(NO$_3$)$_2$; 2.12 parts], 2.17 parts of cerium nitrate [Ce(NO$_3$)$_3$.6H$_2$O] and cobalt nitrate [Co(NO$_3$)$_2$.6H$_2$O] were dissolved in about 100 parts of water, and the solution was added dropwise to about 100 parts of an aqueous solution containing 2.43 parts of sodium carbonate. The resulting precipitate was left to stand overnight, and then decanted with distilled water several times. It was then filtered, and dried at 110° C. overnight. The resulting powder was fired at 600° C. for 3 hours, and the black powder obtained was molded under a pressure of 500 kg/cm². The molded product was fired in the air at 1200° C. for 5 hours. The sintered body obtained was further pulverized and mixed, molded under a pressure of 2 tons/cm², and fired at 1200° C. for 8 hours in the air to give a sintered body having a density of 5.3 g/cm³ and the X-ray (Cu-Kα) diffraction pattern shown in Table 2. The sintered body was a solid electrolyte having an electron conductivity of $25.6 \times 10$ ohm$^{-1}$·cm$^{-1}$ and an oxide ion conductivity of $5.2 \times 10^{-2}$ ohm$^{-1}$·cm$^{-1}$.

A bottomed cylindrical sample of the sintered body having a thickness of 1 mm, an inside diameter of 10 mm and a height of 6 mm was prepared, and an argon gas was caused to flow through the inside of the sample at a flow rate of 30 cc (STP)/min. while keeping its outside in contact with the air. The sample was heated to 800° C. The oxygen concentration in the argon gas flow was determined by gas chromatography. It was ascertained that oxygen permeated through the sample at $1.5 \times 10^{-3}$ cc (STP)/sec·cm².

TABLE 2

| Diffraction angle (2θ) | Relative intensity (%; the peak intensity at 2θ = 29.4 is taken as 100%) |
| --- | --- |
| 29.0 | 12 |

TABLE 2-continued

| Diffraction angle (2θ) | Relative intensity (%; the peak intensity at 2θ = 29.4 is taken as 100%) |
| --- | --- |
| 29.4 | 100 |
| 29.7 | 12 |
| 32.8 | 71 |
| 42.0 | 42 |
| 47.3 | 15 |
| 51.7 | 19 |
| 52.5 | 25 |
| 58.5 | 10 |

EXAMPLE 3

Strontium acetate [Sr(OCOCH$_3$)$_2$.½H$_2$O; 5.37 parts], 11.65 parts of bismuth oxide (Bi$_2$O$_3$) and 6.23 parts of cobalt acetate [Co(OCOCH$_3$)$_2$.4H$_2$O] were pulverized and mixed in a mortar. The mixture was fired at 600° C. for 1 hour, pulverized and mixed, press-formed under a pressure of 500 kg/cm², and fired in the air at 830° C. for 5 hours. The resulting sintered body was further pulverized and mixed, press-formed under a pressure of about 2 tons/cm², and again fired in the air at 830° C. for 8 hours to afford a sintered body having a density of 6.5 g/cm³ and the X-ray (Cu-Kα) diffraction pattern shown in Table 3. The sintered body was a solid electrolyte having an electron conductivity of 9.0 ohm$^{-1}$·cm$^{-1}$ and an oxide ion conductivity of $2.84 \times 10^{-2}$ ohm$^{-1}$·cm$^{-1}$.

A bottomed cylindrical sample of the sintered body having an outside diameter of 12.1 mm, an inside diameter of 9.6 mm, a height of 7.8 mm and a thickness of 1.25 mm was prepared. An argon gas was caused to flow through the inside of the cylindrical sample while keeping its outside in contact with the air. The sample was heated to 800° C., and the oxygen concentration of the argon gas flow was determined by gas chromatography. It was ascertained that oxygen permeated through the sample at $8.94 \times 10^{-4}$ cc (STP)/sec·cm².

TABLE 3

| Diffraction angle (2θ) | Relative intensity (%; the peak intensity at 2θ = 28.2 is taken as 100%) |
| --- | --- |
| 26.1 | 18 |
| 26.7 | 33 |
| 28.2 | 100 |
| 28.8 | 66 |
| 30.0 | 58 |
| 30.4 | 46 |
| 36.4 | 16 |
| 45.8 | 32 |
| 49.4 | 28 |
| 54.8 | 32 |

EXAMPLE 4

Lanthanum oxide (La$_2$O$_3$; 16.291 parts), 8.606 parts of cerium oxide (CeO$_2$) and 12.45 parts of cobalt acetate [Co(OCOCH$_3$)$_2$.4H$_2$O] were pulverized and mixed in a mortar. The mixture was fired at 600° C. for 1 hour, pulverized and mixed, press-formed under a pressure of 500 kg/cm² and then again fired in the air at 1300° C. for 6 hours. The sintered body obtained was again pulverized and mixed, press-formed under a pressure of about 2 tons/cm², and fired in the air at 1300° C. for 10 hours to afford a sintered body having a density of 6.2 g/cm² and the X-ray (Cu-Kα) diffraction pattern shown in Table 4. The sintered body was a solid electrolyte having an electron conductivity of 5.1 ohm$^{-1}$.cm$^{-1}$ and an oxide ion conductivity of 2.26×10$^{-2}$ ohm$^{-1}$.cm$^{-1}$.

A bottomed cylindrical sample of the sintered body having an outside diameter of 12.3 mm, an inside diameter of 10.0 mm, a height of 5.75 mm and a thickness of 1.15 mm was prepared. An argon gas was passed through the inside of the cylindrical sample while keeping its outside in contact with the air. The sample was heated to 800° C. The oxygen concentration of the argon gas was determined by gas chromatography. It was ascertained that oxygen permeated through the sample at 8.46×10$^{-4}$ cc (STP)/sec.cm$^2$.

TABLE 4

| Diffraction angle (2θ) | Relative intensity (%; the peak intensity at 2θ = 27.9 is taken as 100%) |
|---|---|
| 27.9 | 100 |
| 32.2 | 25 |
| 32.8 | 27 |
| 33.2 | 27 |
| 46.3 | 57 |
| 47.4 | 17 |
| 54.9 | 48 |
| 58.9 | 13 |
| 74.5 | 16 |
| 85.8 | 12 |

EXAMPLE 5

Lanthanum oxide (La$_2$O$_3$; 0.652 part), 1.29 parts of strontium acetate [Sr(OCOCH$_3$)$_2$½H$_2$O], 2.49 parts of cobalt acetate [Co(OCOCH$_3$)$_2$.4H$_2$O] and 4.66 parts of bismuth oxide (Bi$_2$O$_3$) were pulverized and mixed in a mortar. The mixture was fired at 600° C. for 1 hour, pulverized and mixed, press-formed under a pressure of 500 kg/cm$^2$, and fired in the air at 900° C. for 8 hours. The sintered body obtained was further pulverized and mixed, press-formed under a pressure of 2 tons/cm$^2$, and again fired in the air at 900° C. for 10 hours to afford a sintered body having a density of 6.7 g/cm$^3$ and the X-ray (Cu-Kα) diffraction pattern shown in Table 5. The sintered body was a solid electrolyte having an electron conductivity of 2.9×10$^{-1}$ ohm$^{-1}$.cm$^{-1}$ and an oxide ion conductivity of 6.7×10$^{-1}$ ohm$^{-1}$.cm$^{-1}$.

A bottomed cylindrical sample of the sintered body having an outside diameter of 12.3 mm, an inside diameter of 11.3 mm, a thickness of 1 mm and a height of 14.3 mm was prepared, and an argon gas was caused to flow through the inside of the sample at a flow rate of 30 cc (STP/min. while keeping its outside in contact with the air. The sample was heated to 800° C. The oxygen concentration of the argon gas flow was determined by gas chromatography. It was ascertained that oxygen permeated through the sample at 1.9×10$^{-3}$ cc (STP)/sec.cm$^2$.

TABLE 5

| Diffraction angle (2θ) | Relative intensity (%; the peak intensity at 2θ = 28.4 is taken as 100%) |
|---|---|
| 26.6 | 17 |
| 28.4 | 100 |
| 28.7 | 41 |
| 30.3 | 23 |
| 33.1 | 8 |
| 40.6 | 3 |
| 47.3 | 6 |
| 58.8 | 14 |

EXAMPLE 6

Lanthanum oxide (La$_2$O$_3$; 2.61 parts), 5.14 parts of strontium acetate [Sr(OCOCH$_3$)$_2$½H$_2$O], 9.96 parts of cobalt acetate [Co(OCOCH$_3$)$_2$.4H$_2$O] and 6.88 parts of cerium oxide (CeO$_2$) were pulverized and mixed in a mortar. The mixture was fired at 600° C. for 1 hour, pulverized and mixed, press-formed under a pressure of 500 kg/cm$^2$, and the fired in the air at 1350° C. for 5 hours. The resulting sintered body was further pulverized and mixed, press-formed under a pressure of 2 tons/cm$^2$, and again fired in the air at 1350° C. for 8 hours to afford a sintered body having a density of 5.1 g/cm$^3$ and the X-ray (Cu-Kα) diffraction pattern shown in Table 6. The sintered body was a solid electrolyte having an electron conductivity of 19.6 ohm$^{-1}$.cm$^{-1}$ and an oxide ion conductivity of 5.7×10$^{-2}$ ohm$^{-1}$.cm$^{-1}$.

A bottomed cylindrical sample of the sintered body having an outside diameter of 12.7 mm, an inside diameter of 10.35 mm, a height of 11.65 mm and a thickness of 1.17 mm was prepared, and an argon gas was caused to flow through the inside of the sample at a constant flow rate while keeping its outside in contact with the air. The sample was heated to 800° C., and the oxygen concentration of the argon gas flow was determined by gas chromatography. It was ascertained that oxygen permeated through the sample at 1.92×10$^{-3}$ cc (STP)/cm$^2$.sec.

TABLE 6

| Diffraction angle (2θ) | Relative intensity (%; the peak intensity at 2θ = 33.0 is taken as 100%) |
|---|---|
| 28.6 | 63 |
| 33.0 | 100 |
| 40.8 | 12 |
| 47.4 | 44 |
| 56.2 | 29 |
| 59.1 | 28 |

What we claim is:

1. A solid electrolyte having high electron conductivity and high oxide ion conductivity, which is composed of a sintered body consisting substantially of
   (a) 5 to 85 mole% of an oxide of cobalt,
   (b) 2 to 70 mole% of an oxide of at least one metal selected from strontium and lanthanum, and
   (c) 13 to 80 mole% of an oxide of at least one metal selected from bismuth and cerium.

2. The solid electrolyte of claim 1 which has an electron conductivity of at least 10$^{-2}$ ohm$^{-1}$.cm$^{-1}$.

3. The solid electrolyte of claim 1 which has an electron conductivity of at least 10$^{-1}$ ohm$^{-1}$.cm$^{-1}$.

4. The solid electrolyte of claim 1 which has an oxide ion conductivity of at least 10$^{-4}$ ohm$^{-1}$.cm$^{-1}$.

5. The solid electrolyte of claim 1 which has an oxide ion conductivity of at least 10$^{-3}$ ohm$^{-1}$.cm$^{-1}$.

6. The solid electrolyte of claim 1 wherein the sintered body consists substantially of
   (a) 10 to 80 mole% of the oxide of cobalt,
   (b) 3 to 60 mole% of the oxide of at least one metal selected from strontium and lanthanum, and
   (c) 15 to 70 mole% of the oxide of at least one metal selected from bismuth and cerium.

7. The solid electrolyte of claim 1 wherein the sintered body consists substantially of
   (a) cobalt oxide,
   (b) lanthanum oxide, and (c) bismuth oxide.

8. The solid electrolyte of claim 1 wherein the sintered body consists substantially of
   (a) 15 to 40 mole% of cobalt oxide,
   (b) 40 to 55 mole% of strontium oxide, and
   (c) 15 to 40 mole% of cerium oxide.

9. The solid electrolyte of claim 7 wherein the sintered body consists substantially of
   (a) 15 to 75 mole% of cobalt oxide,
   (b) 13 to 45 mole% of lanthanum oxide, and
   (c) 17 to 50 mole% of bismuth oxide.

10. A process for producing a solid shaped electrolyte composed of a sintered body consisting substantially of (a) cobalt oxide, (b) at least one of strontium oxide and lanthanum oxide and (c) at least one of bismuth oxide and cerium oxide by the steps of
    forming a mixture consisting substantially of
    (i) cobalt, cobalt oxide, or a cobalt compound capable of being decomposed to cobalt oxide under the below defined firing conditions,
    (ii) at least one of strontium metal, lanthanum metal, strontium oxide, lanthanum oxide and compound of strontium or lanthanum capable of being decomposed to the respective metal oxide of strontium or lanthanum under the below defined firing conditions, and
    (iii) at least one of bismuth metal, cerium metal, bismuth oxide, cerium oxide, and compounds of bismuth or cerium capable of being decomposed to the respective metal oxide of bismuth or cerium under the below defined firing conditions,
    press-forming the mixture into a desired shape, and
    firing the shaped mixture at a temperature of from about 400° C. to about 1400° C. in an oxygen-containing gas atmosphere, wherein said mixture contains components (i), (ii), and (iii) in such proportions as to provide the respective oxides of (a), (b) and (c) in mole percentages of 5 to 85 mole%, 2 to 70 mole% and 13 to 80 mole%, respectively.

* * * * *